United States Patent
Chechik

(10) Patent No.: US 9,308,088 B2
(45) Date of Patent: *Apr. 12, 2016

(54) ARTIFICIAL URINARY SPHINCTER SYSTEM DEFLATION ASSEMBLY

(71) Applicant: Joel Craig Chechik, Minneapolis, MN (US)

(72) Inventor: Joel Craig Chechik, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 186 days.

This patent is subject to a terminal disclaimer.

(21) Appl. No.: 13/901,876

(22) Filed: May 24, 2013

(65) Prior Publication Data

US 2013/0261386 A1    Oct. 3, 2013

Related U.S. Application Data

(63) Continuation-in-part of application No. 13/425,443, filed on Mar. 21, 2012, now Pat. No. 8,491,462, which is a continuation of application No. 13/204,749, filed on Aug. 8, 2011, now Pat. No. 8,684,910.

(30) Foreign Application Priority Data

Aug. 8, 2011    (DK) .................................. 2011 70435
Aug. 7, 2012    (WO) ................. PCT/DK2012/000090

(51) Int. Cl.
    *A61F 2/26*    (2006.01)
(52) U.S. Cl.
    CPC .......................................... *A61F 2/26* (2013.01)
(58) Field of Classification Search
    CPC ..... Y10S 128/25; Y10S 128/26; A61F 2/004; A61F 2250/0098
    USPC .................................... 600/29–32, 37, 38–41
    See application file for complete search history.

(56) References Cited

U.S. PATENT DOCUMENTS 3,744,063 A     7/1973   McWhorter et al.
3,863,622 A *   2/1975   Buuck ............................ 600/31

(Continued)

FOREIGN PATENT DOCUMENTS

EP     0093507       11/1983
FR     2856582 A1    12/2004

(Continued)

OTHER PUBLICATIONS

American Medical Systems, AMS 800TM Urinary Control System Operating Room Manual, 2004.

*Primary Examiner* — Samuel Gilbert
(74) *Attorney, Agent, or Firm* — Coloplast Corp., Coloplast A/S; Nick Baumann

(57) ABSTRACT

An artificial urinary sphincter system includes a cuff implantable around a portion of a urethra, an implantable pressure-regulating reservoir, and a deflation assembly attachable between the cuff and the implantable pressure-regulating reservoir. The deflation assembly includes a valve that selectively restricts movement of the fluid from the cuff to the pressure-regulating reservoir, a base and an activation surface opposite the base. The activation surface includes an outer peripheral rim surrounding a pad that is movable to displace the valve to allow the fluid to flow from the cuff to the pressure-regulating reservoir. An entirety of the pad is recessed relative to the outer peripheral rim such that the outer peripheral rim defines a maxima of the activation surface.

19 Claims, 13 Drawing Sheets

(56) References Cited

U.S. PATENT DOCUMENTS

| | | | |
|---|---|---|---|
| 4,063,548 | A | 12/1977 | Klatt et al. |
| 4,191,196 | A | 3/1980 | Bradley et al. |
| 4,222,377 | A | 9/1980 | Burton |
| 4,412,530 | A | 11/1983 | Burton |
| 4,517,967 | A | 5/1985 | Timm et al. |
| 4,522,198 | A | 6/1985 | Timm et al. |
| 4,559,931 | A | 12/1985 | Fischell |
| 4,724,830 | A | 2/1988 | Fischell |
| 4,784,660 | A | 11/1988 | Fischell |
| 4,878,889 | A | 11/1989 | Polyak |
| 4,909,785 | A | 3/1990 | Burton et al. |
| 4,932,956 | A | 6/1990 | Reddy et al. |
| 4,932,958 | A | 6/1990 | Reddy et al. |
| 4,994,020 | A | 2/1991 | Polyak |
| 5,012,822 | A | 5/1991 | Schwarz |
| 5,048,511 | A * | 9/1991 | Rosenbluth et al. ............ 600/40 |
| 5,078,720 | A | 1/1992 | Burton et al. |
| 5,254,092 | A | 10/1993 | Polyak |
| 5,335,669 | A | 8/1994 | Tihon et al. |
| 5,356,423 | A | 10/1994 | Tihon et al. |
| 5,496,271 | A | 3/1996 | Burton et al. |
| 5,499,994 | A | 3/1996 | Tihon et al. |
| 5,518,504 | A | 5/1996 | Polyak |
| 5,720,415 | A | 2/1998 | Morningstar |
| 5,895,356 | A | 4/1999 | Andrus et al. |
| 6,171,233 | B1 | 1/2001 | Willard |
| 6,382,214 | B1 | 5/2002 | Raz et al. |
| 6,460,262 | B1 | 10/2002 | Cabak et al. |
| 6,558,315 | B1 | 5/2003 | Kuyava |
| 6,612,977 | B2 | 9/2003 | Staskin et al. |
| 6,616,653 | B2 | 9/2003 | Beyar et al. |
| 6,652,450 | B2 | 11/2003 | Neisz et al. |
| 6,802,807 | B2 | 10/2004 | Anderson et al. |
| 6,971,986 | B2 | 12/2005 | Staskin et al. |
| 6,991,601 | B2 | 1/2006 | Kuyava et al. |
| 7,015,253 | B2 | 3/2006 | Escandon et al. |
| 7,048,682 | B2 | 5/2006 | Neisz et al. |
| 7,083,568 | B2 | 8/2006 | Neisz et al. |
| 7,267,645 | B2 | 9/2007 | Anderson et al. |
| 7,291,104 | B2 | 11/2007 | Neisz et al. |
| 7,315,762 | B2 | 1/2008 | Mosher et al. |
| 7,946,975 | B2 | 5/2011 | George et al. |
| 7,996,092 | B2 | 8/2011 | Mrva et al. |
| 8,062,209 | B2 | 11/2011 | Rowland et al. |
| 8,491,462 | B2 | 7/2013 | Chechik |
| 8,684,910 | B2 | 4/2014 | Chechik |
| 8,740,769 | B2 * | 6/2014 | Chechik ......................... 600/40 |
| 2013/0041213 | A1 | 2/2013 | Chechik |
| 2014/0155691 | A1 | 6/2014 | Chechik |

FOREIGN PATENT DOCUMENTS

| | | |
|---|---|---|
| GB | 2355937 A1 | 5/2001 |
| WO | 2013020555 A2 | 2/2013 |

* cited by examiner

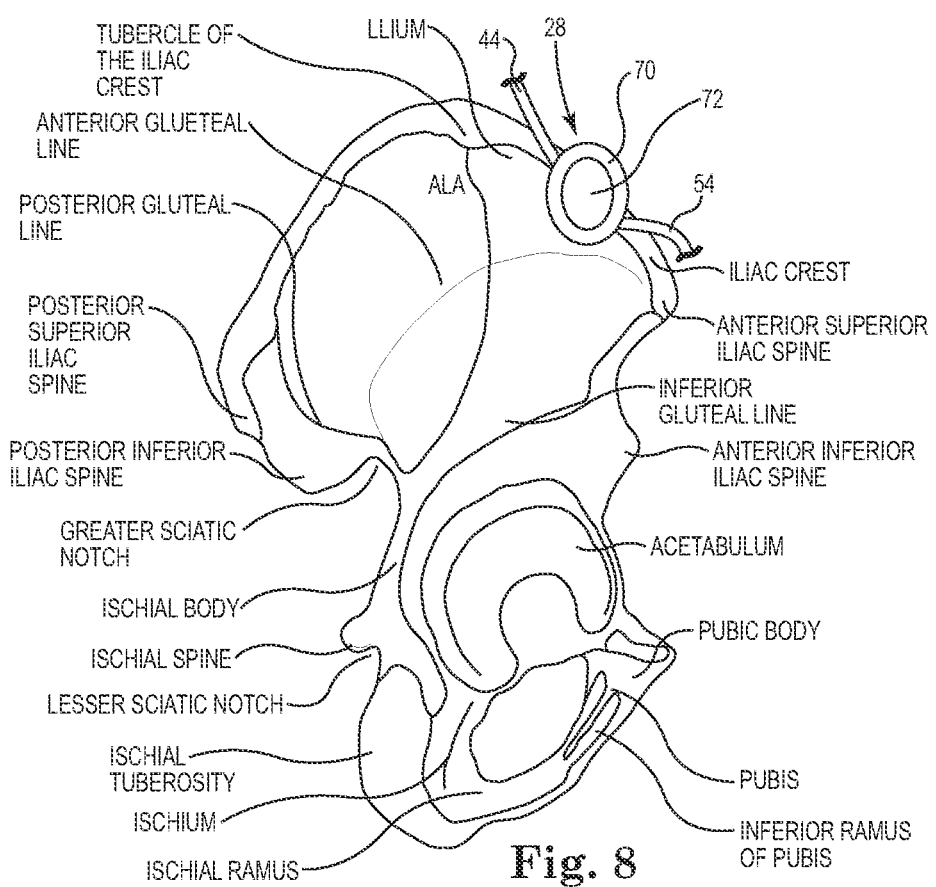

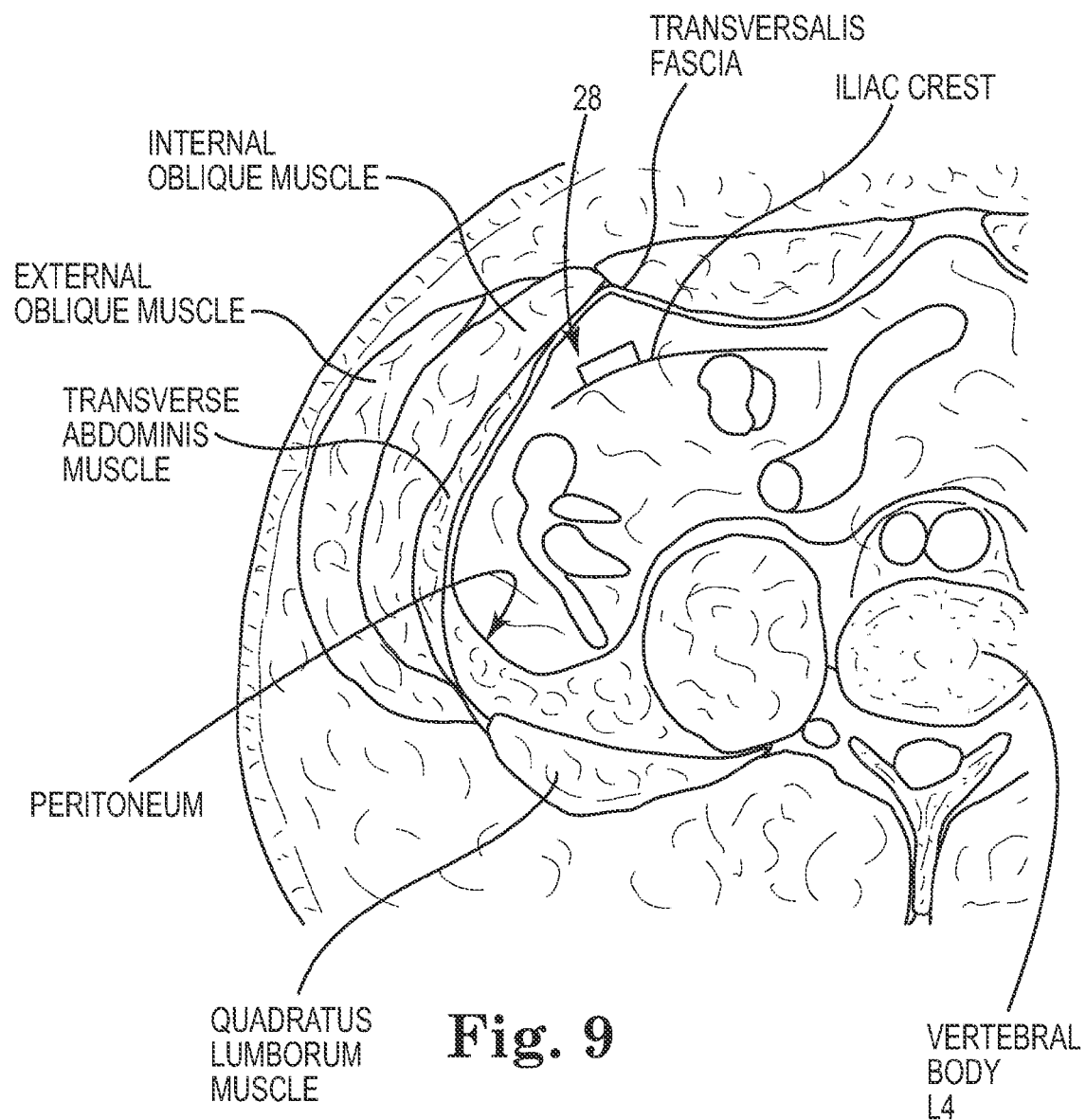

ARTIFICIAL URINARY SPHINCTER SYSTEM DEFLATION ASSEMBLY

BACKGROUND

An implanted penile prosthetic is effective in relieving erectile dysfunction in men.

A penile prosthetic typically includes one or more cylinders that are implanted in the corpora cavernosa of the penis, a reservoir implanted in the abdomen that communicates with the cylinder(s), and a pump located in the scrotum that is employed to move liquid from the reservoir into the cylinder(s).

In a typical application, the user squeezes a bulb of the pump multiple times to draw liquid out of the reservoir, into the bulb, and move the liquid into the cylinders. The repeated squeezing of the bulb moves the liquid from the reservoir into the cylinders, which incrementally deflates the reservoir and incrementally inflates the cylinder(s) to eventually provide the user with an erect penis. The user may return the penis to its flaccid state by activating a release mechanism associated with the pump to selectively transfer the liquid from the cylinder(s) back into the reservoir.

The above-described penile prosthetics have proven effective in relieving erectile dysfunction in men. However, there is a desire for improved penile prosthetic devices.

SUMMARY

One aspect provides an artificial urinary sphincter system including a cuff, an implantable pressure-regulating reservoir, and a deflation assembly. The cuff is implantable around a portion of a urethra. The deflation assembly is attachable between the cuff and the implantable pressure-regulating reservoir. The deflation assembly includes a valve that selectively restricts movement of the fluid from the cuff to the pressure-regulating reservoir, a base, and an activation surface opposite the base. The activation surface includes an outer peripheral rim surrounding a pad that is movable to displace the valve to allow the fluid to flow from the cuff to the pressure-regulating reservoir. An entirety of the pad is recessed relative to the outer peripheral rim such that the outer peripheral rim defines a maxima of the activation surface.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 8 is a side view of a pelvis showing the deflation assembly illustrated in FIG. 1 implanted against an iliac crest of the pelvis.

FIG. 9 is a top view of a pelvis showing the deflation assembly illustrated in FIG. 1 implanted between transversalis fascia and an exterior surface of the pelvis.

DETAILED DESCRIPTION

Figure 1:
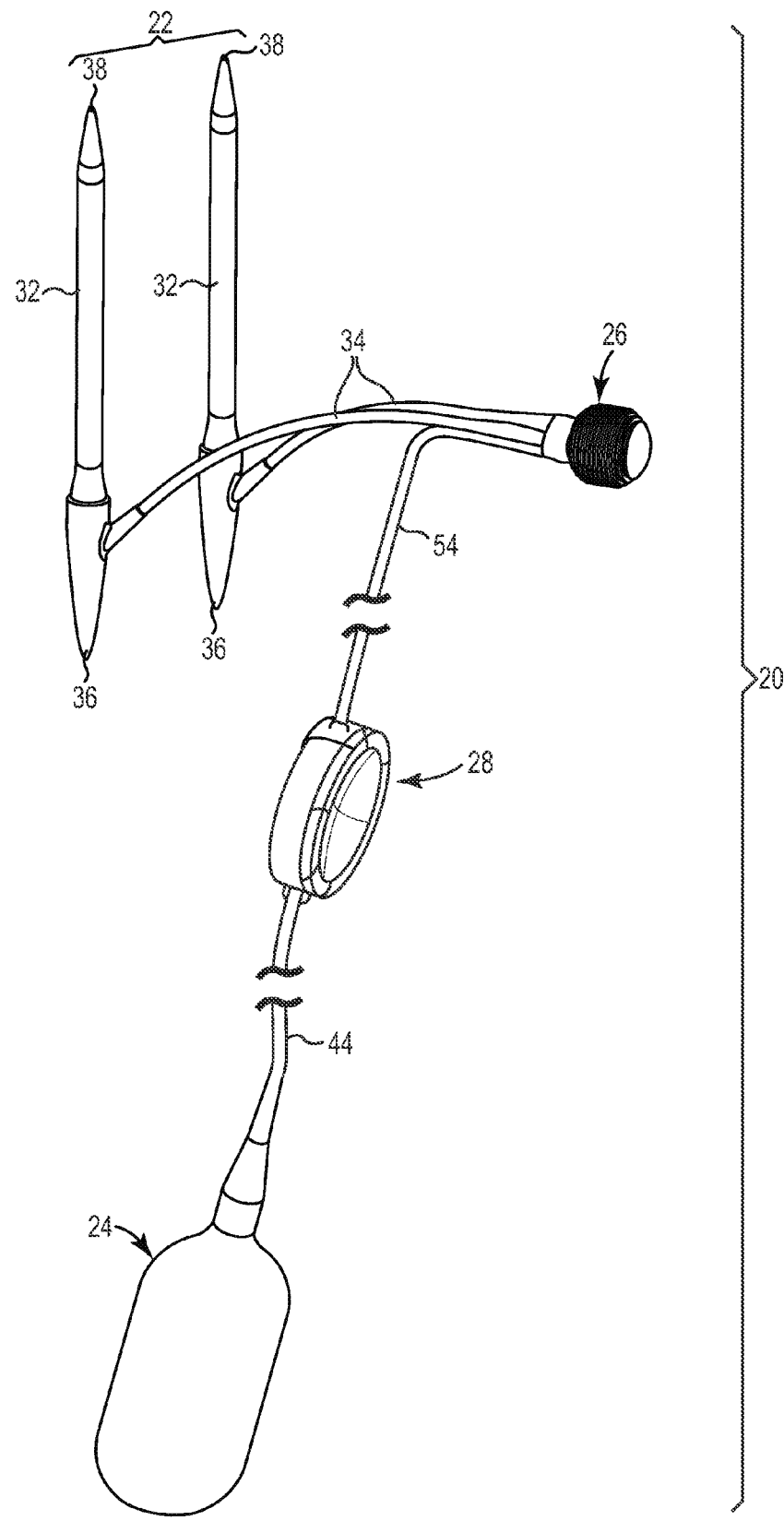
FIG. 1 is a perspective view of one embodiment of a penile prosthetic including a reservoir, a pump, and a deflation assembly separate from the reservoir and the pump.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

"Fluid" means a non-solid substance that flows and includes gases and liquids, or a combination of a gas and a liquid.

"Gas" means a substance having molecules that disperse and are free to expand to occupy an entire volume of a container in which it is disposed. Air and methyl butane are two examples of gases.

"Liquid" means a substance having molecules that do not disperse such that the liquid resists compression and the molecules of the liquid will not disperse to fill all spaces of a container in which the liquid is disposed. Saline is an example of a liquid.

"Maxima" means the point that is a maximum distance away from a surface. In this specification, a deflation assembly provides an activation surface that includes an outer peripheral rim surrounding an activation area, and the activation area is recessed in a concave configuration relative to the outer peripheral rim such that the outer peripheral rim is a maxima of the activation surface.

Ectopic refers to the placement of a penile prosthetic deflation assembly between fascia and an exterior surface of a pelvis of the patient.

Embodiments provide a penile prosthetic having a deflation assembly that is easily identifiable to allow the patient to locate and activate (i.e., palpate) the deflation assembly. The deflation assembly is provided separately from the reservoir and separately from the pump to allow the functional aspects of the pump and the deflation assembly to be decoupled. This permits the pump to be manufactured in a smaller than usual and allows the deflation assembly to be customized based on patient anatomy.

A penile prosthetic deflation assembly is usually implanted in a scrotum of the patient, where the thin skin of the scrotum allows for easy palpation of the deflation assembly. However, some patients do not have the dexterity to operate a deflation assembly that is implanted in the scrotum.

Some penile prosthetic devices include a deflation assembly incorporated with the pump. The pump is typically implanted in the scrotum of the patient. It has been observed that the pump can rotate after it is implanted. It is difficult for the user to locate the deflation mechanism incorporated into the pump if the pump rotates. Embodiments provide a deflation mechanism that is separate from the pump where the deflation mechanism includes a prominent and easily identifiable activation surface that is even identifiable through the skin and fat tissue layers of clinically obese users.

FIG. 1 is a perspective view of one embodiment of an assembled penile prosthetic 20. The penile prosthetic 20 includes a penile implant 22, a reservoir 24, a pump 26, and a deflation assembly 28. Each of the two illustrated penile implants 22 provides a "cylinder" that is implanted in a corpora cavernosum within the shaft of the penis. The reservoir 24 retains a fluid that is employed to inflate the penile implant 22. The pump 26 is connected between the penile implant 22 and the reservoir 24 and operates to move the fluid from the reservoir 24 to the penile implant 22 to inflate the penile implant 22 to an erect state. The deflation assembly 28 functions to selectively restrict movement of the fluid from the penile implant 22 to the reservoir 24 to ensure that the penile implant 22 remains erect when inflated. In addition, the deflation assembly 28 functions to selectively move the fluid from the penile implant 22 back to the reservoir 24 to deflate the penile implant 22 to a flaccid state. The deflation assembly 28 provides a prominent activation surface (described below) that is easily palpated by the user.

In one embodiment, the penile implant 22 includes a pair of inflatable cylinders 32 that are sized to be implanted into the penis, and each of the cylinders 32 is connected to the pump 26 by tubes 34. The tubes 34 are preferably kink-resistant. Each of the cylinders 32 includes a proximal end 36 opposite a distal end 38. During implantation, the proximal end 36 (also called a rear tip) is implanted toward the crus of the penis and the distal end 38 is implanted within the glans penis. The cylinders 32 are fabricated from material configured to collapse and be flexible when the cylinders 32 are deflated to provide the penis with a comfortable flaccid state and expand when the cylinders 32 are inflated with liquid to provide the penis with an erection. Suitable material for fabricating the cylinders 32 includes silicone, polymers such as urethanes, blends of polymers with urethane, or copolymers of urethane, or the like. Suitable cylinders are available from Coloplast Corp., Minneapolis, Minn.

The reservoir 24 is sized to hold a volume of liquid between about 50-350 ml and is connected to the deflation assembly 28 by a tube 44. The tube 44 is preferably kink-resistant. In one embodiment, the reservoir 24 is provided as a cylindrical reservoir formed from an elastic, flexible polymer with a wall thickness of between 0.005-0.060 inches. In one embodiment, the reservoir 24 is provided as a "cloverleaf" style of reservoir having multiple leaves that may be folded one against the other to compactly fold the reservoir 24 for implantation into the abdomen of the user. The reservoir 24 is fabricated from material suitable for body implantation, such as silicone or the urethane-based materials described above for the cylinders 32. One suitable reservoir 24 is sized to contain approximately 130 ml of liquid and is available from Coloplast Corp., Minneapolis, Minn.

The pump 26 generally includes a bulb or other mechanism provided to move the fluid in the reservoir 24 to the penile implant 22. The pump 26 is provided with a pair of inflation ports 44 that connect with the cylinders 32 via the tubes 34 and can include one or more suitable valve assemblies configured to check or limit the flow of the fluid to the cylinders 32. The pump 26 is fabricated from material suitable for body implantation, such as silicone or the urethane-based materials described above for the cylinders 32.

The deflation assembly 28 is separate from the reservoir 24 and separate from the pump 26 and is connected between the pump 26 and the reservoir 24 by a tube 54. The tube 54 is preferably kink-resistant.

Figure 2:
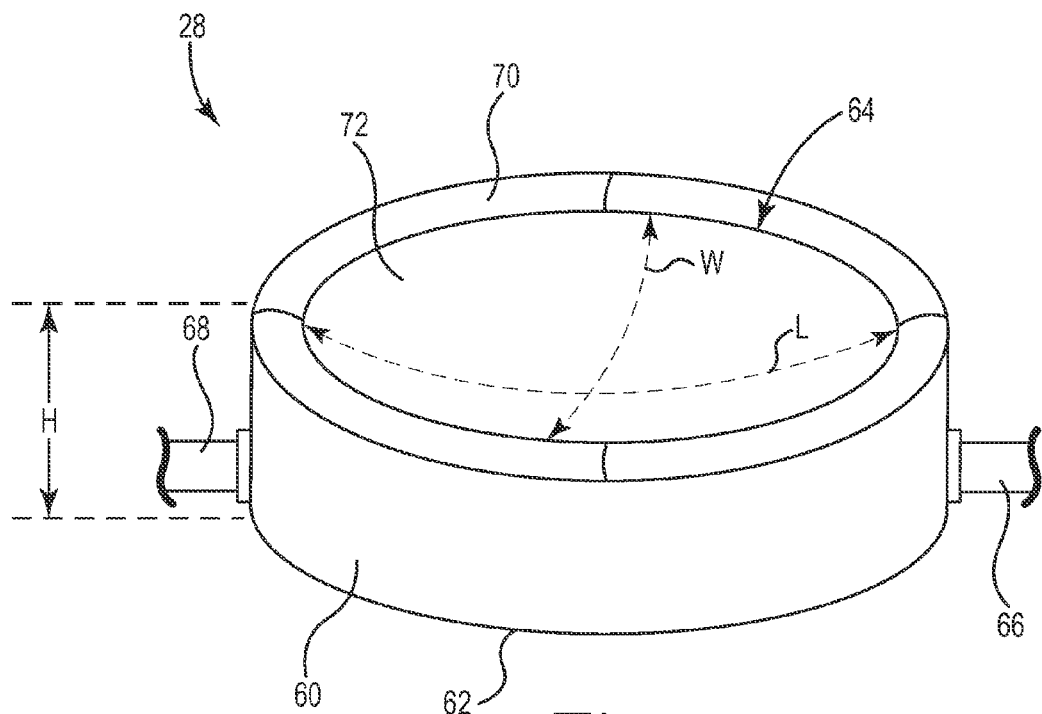
FIG. 2 is a perspective view of one embodiment of the deflation assembly illustrated in FIG. 1.
Figure 3:
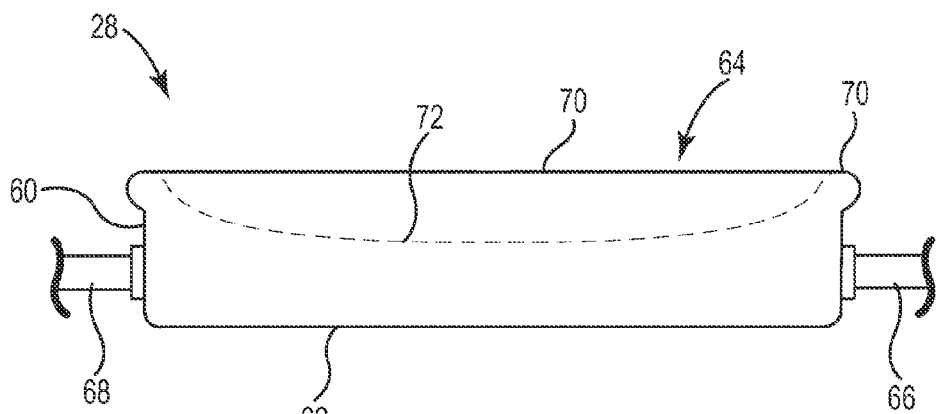
FIG. 3 is a side view of the deflation assembly illustrated in FIG. 2.
Figure 4:
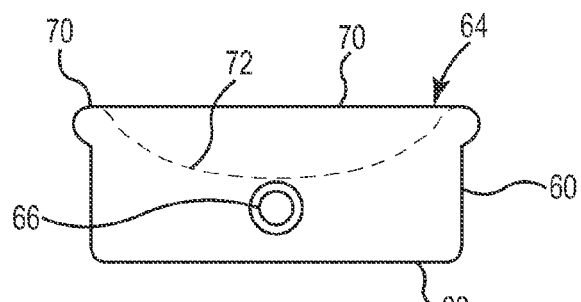
FIG. 4 is an end view of the deflation assembly illustrated in FIG. 2.

FIG. 2 is a perspective view, FIG. 3 is a side view, and FIG. 4 is an end view of one embodiment of the deflation assembly 28. The deflation assembly 28 includes a side surface 60 extending between a base 62 and activation surface 64. In one embodiment, the side surface 60 includes an inlet port 66 that communicates with the reservoir 24 and an outlet port 68 that communicates the penile implant 22 (FIG. 1). The activation surface 64 includes an outer peripheral rim 70 surrounding an activation area 72. The activation area 72 is recessed in a concave configuration relative to the outer peripheral rim 70 such that the outer peripheral rim 70 defines a maxima of the activation surface 64 (best illustrated in FIGS. 3 and 4). The activation area 72 provides a pad 72 that is central to the activation surface 64. In one embodiment, the activation area 72 (or pad 72) is entirely located between the outer peripheral rim 70 and the base 62.

The rim 70 protects the activation area 72 from unintended activation. The rim 70 is configured to be hard or immovable and easily identifiable even through skin and tissue. The rim 70 provides a landmark that once located directs the user to the location of the pad 72. The rim 70 is thus easily palpatable, but pushing on the rim 70 will not activate the deflation mechanism of the assembly 28. The pad 72 is movable and protected by the rim 70, but the pad 72 is easy to push once the rim 70 is located.

The activation area 72 is movable, and in one embodiment is fabricated from a polymer that is configured to be more flexible than the outer peripheral rim 70. In one embodiment, the outer peripheral rim 70 is harder (i.e., has a higher durometer) than the activation area 72. In one embodiment, the activation area 72 is movable and the outer peripheral rim 70 is immovable.

The deflation assembly 28 generally encloses a valve or some sort of valve assembly (FIG. 5) that is located between the inlet port 66 and the outlet port 68. The valve is provided to selectively restrict movement of the fluid from the penile implant 22 to the reservoir 24 when the penile implant 22 is erect. The activation surface 64, and in particular the activation area 72, is operable to displace the valve to allow movement of the fluid from the penile implant 22 back to the reservoir 24 to return the penile implant 22 to a flaccid state.

In one embodiment, the activation area 72 is movable toward the base 62 to move a position of the valve. In one embodiment, the outer peripheral rim 70 is substantially immovable and provides a hard, easily palpatable surface for access by the user.

In one embodiment, the base 62 is a lower surface and the activation surface 64 is an upper surface of the deflation assembly 28. The activation surface 64 provides a length L and a width W, and the side surface 60 provides a height H. In one embodiment, the length L of the activation surface 64 is larger than the height H of the side surface 60. In one embodiment, the width W of the activation surface 64 is larger than the height H of the side surface 60. In one embodiment, the length L and the width W of the activation surface 64 are each larger than the height H a side surface 60.

Figure 5:
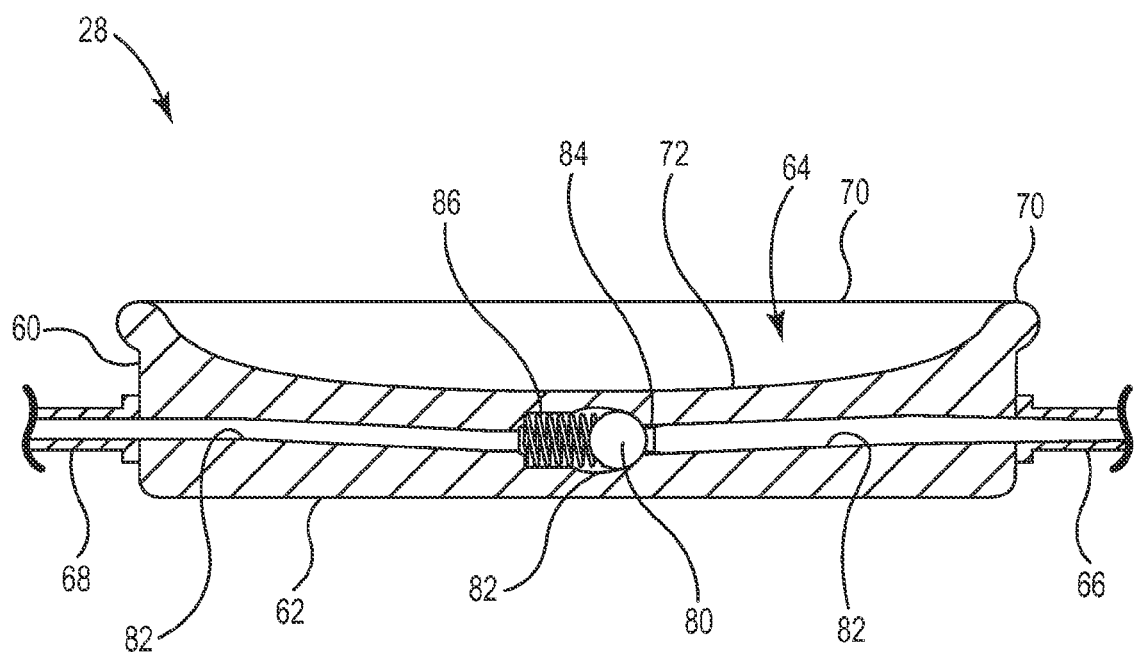
FIG. 5 is a cross-sectional view of one embodiment of the deflation assembly illustrated in FIG. 3.

FIG. 5 is a cross-sectional view of the deflation assembly 28. The deflation assembly 28 encloses a valve 80 that is disposed within a flow path 82. The flow path 82 extends between the inlet port 66 and the outlet port 68. In one embodiment, the valve 80 is a ball valve that is biased to seat against a valve seat 84 by a spring 86.

With reference to FIG. 1, when the pump 26 is repeatedly squeezed it draws fluid from the reservoir 24. The fluid drawn out of the reservoir 24 displaces the valve 80 off of the valve seat 84 to allow the fluid to flow through the flow path 82 and out of the outlet port 68 to the penile implant 22. When the suction provided by the pump 26 is reduced, for example between squeezes of the pump or when the penile implant 22 is inflated, the spring 86 forces the valve 80 against the valve seat 84 and restricts movement of the fluid from the penile implant 22 back to the reservoir 24. In one embodiment, the activation area 72 is movable and when pressed operates to displace the valve 80 off of the valve seat 84 to allow the fluid in the penile implant 22 to return to the reservoir 24, which deflates penile implant 22.

In one embodiment, the deflation assembly 28 is fabricated from polymer and integrally surrounds the valve 80, the spring 86, and the flow path 82. In one embodiment, the deflation assembly 28 is molded from silicone as a monolithic and integral unit that encloses the valve 80.

In one embodiment, the activation area 72 is provided as a diaphragm flap that extends from the rim 70, and the diaphragm flap is movable to displace the valve 80 away from the seat 84 to allow fluid to pass through the flow path 82.

Figure 6:
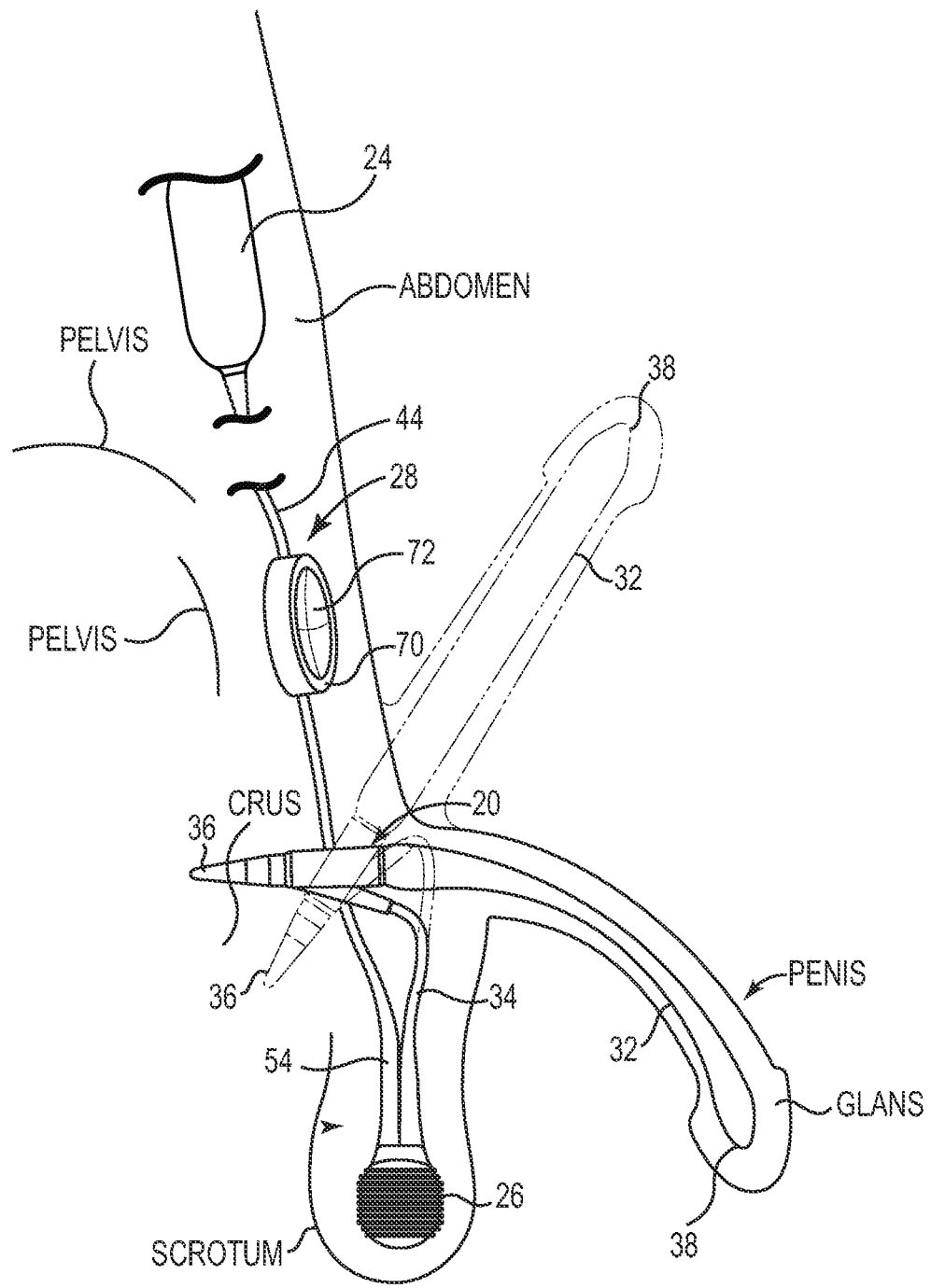
FIG. 6 is a schematic view of one embodiment of the penile prosthetic illustrated in FIG. 1 implanted in a man

FIG. 6 is a schematic view of one embodiment of the penile prosthetic 20 implanted in a man The cylinders 32 are each implanted into one of adjacent corpora cavernosum of the penis with the proximal end 36 implanted into the crus of the penis and the distal end 38 implanted into the glans penis. The reservoir 24 is implanted in the abdomen, either in front of or behind the pubic bone based on the surgeon's preference. The pump 26 is implanted in the scrotum. The deflation assembly 28 is connected between the reservoir 24 and the pump 26 and is implanted under the skin in front of (i.e., exterior to) the pelvis. Suitable locations for implantation of the deflation assembly 28 include between the transversalis fascia and an exterior surface of the pelvis, or behind the puborectalis muscle of the patient. Other suitable locations for implantation of the deflation assembly 28 include placing the base 62 of the deflation assembly 28 against an iliac fossa of the pelvis, or against an iliac crest of the pelvis, or against the pelvis between an anterior gluteal line and an iliac crest of the pelvis.

During use, the pump 26 is repeatedly squeezed to draw fluid from the reservoir 24 through the deflation assembly 28 and into the cylinders 32 implanted in the penis to move the penis from a flaccid state (solid lines) to an erect state (dotted lines). The valve 80 (FIG. 5) prevents the fluid from leaving the cylinders 32 and moving back into the reservoir 24. The user presses on the activation area 72 of the deflation assembly 28 to selectively transfer the fluid in the cylinders 32 back to the reservoir 24 to move the penis from the erect state to the flaccid state. In this regard, the deflation assembly 28 is placed between transversalis fascia and an exterior surface of a pelvis of the patient and the outer peripheral rim 70 is configured to allow the patient to easily feel and locate the activation area 72.

Other existing penile prosthetic devices associate the deflation assembly with the pump that is implanted and accessible in the scrotum, or with the reservoir that is implanted and accessible in the abdomen. However, the pump implanted in the scrotum can rotate over time or through use, which can make locating the deflation assembly difficult. Likewise, the reservoir implanted in the abdomen can move or shift, which makes locating the deflation assembly difficult. In addition, some patients have additional skin folds or a layer of fatty tissue in the abdominal region, which can present challenges to the user in locating the deflation assembly. In contrast, the deflation assembly described herein provides an activation surface having an outer peripheral rim that defines a maxima of the activation surface, which makes the deflation assembly easy to palpate (locate) and use. Specifically, the outer peripheral rim 70 is configured to allow a user to palpate through the skin and fatty tissues to locate the activation area.

Some penile prosthetic devices have a "low profile" reservoir that is designed to provide a minimal depth to reduce or eliminate the visibility of the reservoir when it is implanted. For example, this style of low profile reservoir allows the reservoir to be implanted in front of the puborectalis muscle and behind the abdominal fascia in a location that is not noticeable from an external view of the patient. If such a reservoir would be modified to include a deflation assembly, the deflation assembly would likewise be hidden from view and likely difficult to locate/palpate/identify. In direct contrast, the deflation assembly described herein provides an activation surface having an outer peripheral rim that is easily identifiable when the deflation assembly is placed between transversalis fascia and an exterior surface of a pelvis of the patient.

Figure 7:
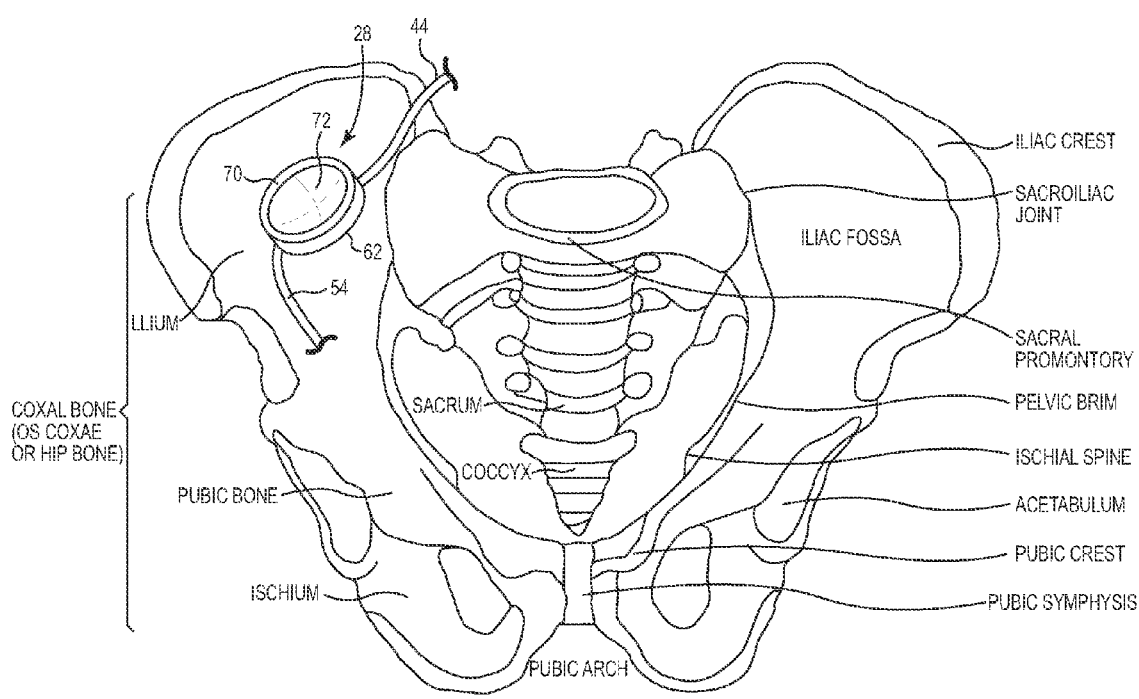
FIG. 7 is a front view of a pelvis showing the deflation assembly illustrated in FIG. 1 implanted against an iliac fossa of the pelvis.

FIG. 7 is a front view of a pelvis showing the deflation assembly 28 implanted against an iliac fossa of the pelvis. The base 62 of the deflation assembly 28 is placed against the iliac fossa with the tube 44 extending to the reservoir 24 and the tube 54 extending to the pump 26. In this location, the deflation assembly 28 is located between the transversalis fascia and an exterior surface of the pelvis. The base 62 is thus placed against the hard surface of the iliac fossa and the outer peripheral rim 70 is easy to locate, which makes the activation area 72 easily palpatable.

FIG. 8 is a side view of a pelvis showing the deflation assembly 28 implanted against an iliac crest of the pelvis. The base 62 of the deflation assembly 28 is located against the iliac crest with the tube 44 extending to the reservoir 24 and the tube 54 extending to the pump 26. In one embodiment, the base 62 of the deflation assembly 28 is placed against the pelvis between an anterior gluteal line and an iliac crest of the pelvis as illustrated. The base 62 is thus placed against the hard surface of the iliac crest and the outer peripheral rim 70 is easy to locate, which makes the activation area 72 easily palpatable.

FIG. 9 is a top view of a pelvis showing the deflation assembly 28 implanted between transversalis fascia and an exterior surface of the pelvis. In particular, the deflation assembly 28 is located against the iliac crest of the pelvis and behind the transversalis fascia.

In one embodiment, the deflation assembly 28 is implanted behind a puborectalis muscle of the patient.

Embodiments thus provide implantation of a deflation assembly such that the outer peripheral rim 70 is distal the pelvis.

Figure 10A:
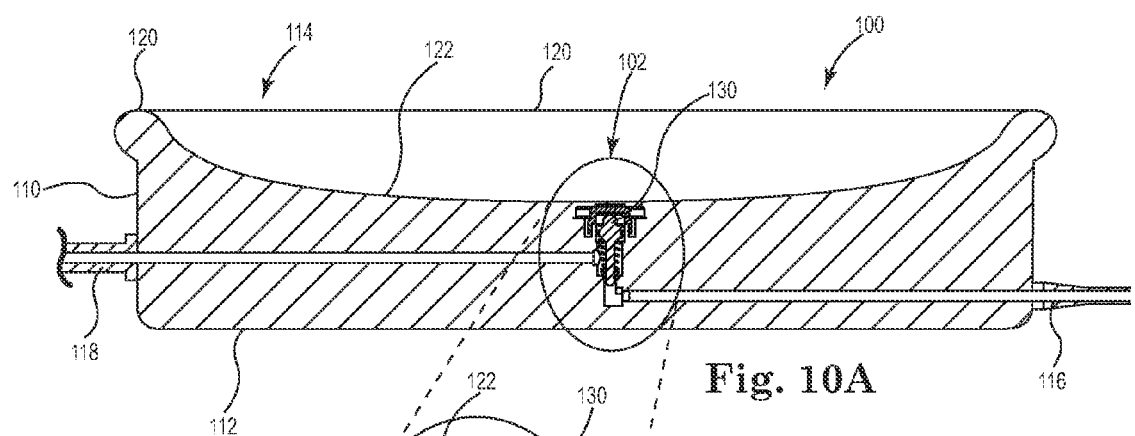
FIG. 10A is a cross-sectional view of one embodiment of a penile prosthetic deflation assembly.
Figure 10B:
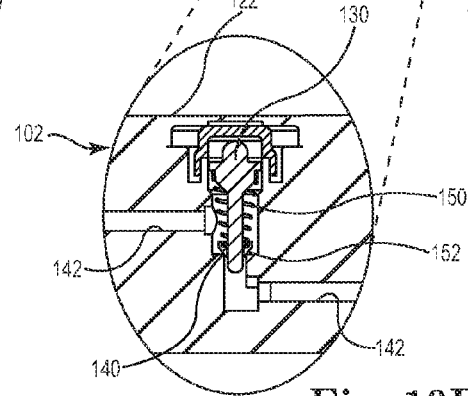
FIG. 10B is a cross-sectional view of one embodiment of a valve assembly of the deflation assembly illustrated in FIG. 10A.

FIG. 10A is a cross-sectional view of one embodiment of a penile prosthetic deflation assembly 100 and FIG. 10B is a cross-sectional view of a valve assembly 102 of the deflation assembly 100. The deflation assembly 100 is operable with the kind of prosthetic described above, and is for example connected between the reservoir 24 and the pump 26 (FIGS. 1 and 6) to operate the penile implant 22.

The deflation assembly 100 includes a side surface 110 extending between a base 112 and activation surface 114. In one embodiment, the side surface 110 includes an inlet port 116 that communicates with the reservoir 24 and an outlet port 118 that communicates the penile implant 22 (FIG. 1). The activation surface 114 includes an outer peripheral rim 120 surrounding an activation area 122. The activation area 122 is recessed in a concave configuration relative to the outer peripheral rim 120 such that the outer peripheral rim 120 defines a maxima of the activation surface 114.

In one embodiment, the deflation assembly 100 encloses a stem valve 130 of the valve assembly 102 that is located between the inlet port 116 and the outlet port 118. The stem valve 130 is provided to selectively restrict movement of the fluid from the penile implant 22 to the reservoir 24 (FIG. 1) when the penile implant 22 is erect. The activation surface 114, and in particular the activation area 122, is operable to displace the valve 130 to allow movement of the fluid from the penile implant 22 back to the reservoir 24 to return the penile implant 22 to a flaccid state.

In one embodiment, the activation area 122 is movable toward the base 112 to move a position of the valve 130. In one embodiment, the outer peripheral rim 120 is substantially immovable and provides a hard, easily palpatable surface accessible by the user.

FIG. 10B illustrates one embodiment in which the stem valve 130 is shaped as a prong that extends from the activation area 122 toward the base 112 and is movable and so configured to displace an interface 140 between the valve 130 and a flow path 142 in which the valve 130 is seated. In one embodiment, the stem valve 130 includes a spring 150 that biases a check valve 152 into engagement with the interface 140.

With additional reference to FIG. 1, repeated squeezing of the pump 26 causes fluid to be drawn from the reservoir 24 through the inlet port 116 (FIG. 10A), which displaces the check valve 152 and compresses the spring 150, to move the check valve 152 off of the interface 140 to allow the fluid to flow through the flow path 142, out of the outlet port 118, and into to the implant 22.

Artificial Urinary Sphincters

Urinary incontinence affects about 200 million people worldwide and about 25 million people in the US. Urinary incontinence is generally more prevalent in women than in men.

Urinary incontinence in women can be associated with a prolapse of one or more pelvic organs, which can arise from a weakness in the tissues/muscle of the pelvic floor. Urinary incontinence in men can arise after surgical treatment of the prostate glade, which treatment can include removal or weakening of the prostatic sphincter associated with the urinary urethra.

One treatment for urinary incontinence includes placing an artificial sphincter around a portion of the urethra. The artificial sphincter has a closed position that selectively prevents the flow of urine through the urethra, thus providing the user with a comfortable, continent state. The artificial sphincter can be activated to an open position by the user, which opens the urethra and allows the user to selectively pass urine.

Surgeons and patients would welcome advances in the treatment of urinary incontinence.

One urinary control system that has found favor with the medical community includes three components cooperatively attached with kink-resistant tubing: an occlusive cuff, a control pump, and a pressure-regulating balloon reservoir. The cuff is implanted around the urethra. The control pump is implanted in the scrotum of a male user. The pressure-regulating balloon reservoir is implanted in the prevesical space, for example through a suprapubic incision followed by dissection of the rectus fascia and a spreading of the linea alba. The three components are filled with liquid (saline) to provide a liquid-filled closed system maintained at an equilibrium pressure that closes the cuff around the urethra. When the user wishes to void, he squeezes and releases the pump several times to move fluid from the cuff into the pressure-regulating balloon reservoir. The cuff "deflates" and opens, which allows the urethra to open and pass urine. The pressure-regulating balloon reservoir, having been pressurized to a pressure above the equilibrium pressure by action of the pump, eventually automatically re-pressurizes the cuff to the equilibrium pressure over the course of several minutes to again inflate the cuff and coapt the urethra.

Embodiments described in this application provide an artificial urinary sphincter system having a cuff implantable around a portion of a urethra, an implantable pressure-regulating reservoir, and a deflation assembly attachable between the cuff and the implantable pressure-regulating reservoir. The pressure-regulating reservoir is to be implanted against the hard surface of the exterior pelvis (i.e., the iliac crest or the iliac fossa) such that the outer peripheral rim 70 is easy to locate, which makes the activation area 72 easily palpatable even for those users who have increased body mass or diminished dexterity. Activation of the activation area 72 (by a simple pressing motion with the fingers) followed by pressure applied to the cuff will deflate the cuff and allow the user to pass urine. In other words, pressing the activation area 72 and applying pressure to the cuff will increase the pressure in the reservoir and deflate the cuff. A subsequent second activation of the activation area 72 will allow the pressure to equalize between the reservoir and the cuff, which re-pressurizes the cuff and coapts the urethra.

Thus, embodiments provide an improved artificial urinary sphincter system that does not have a pump mechanism, and an improved artificial urinary sphincter system that has a deflation assembly that is ectopically located between fascia and an exterior surface of a pelvis of the patient for ease of access by the user.

Figure 11:
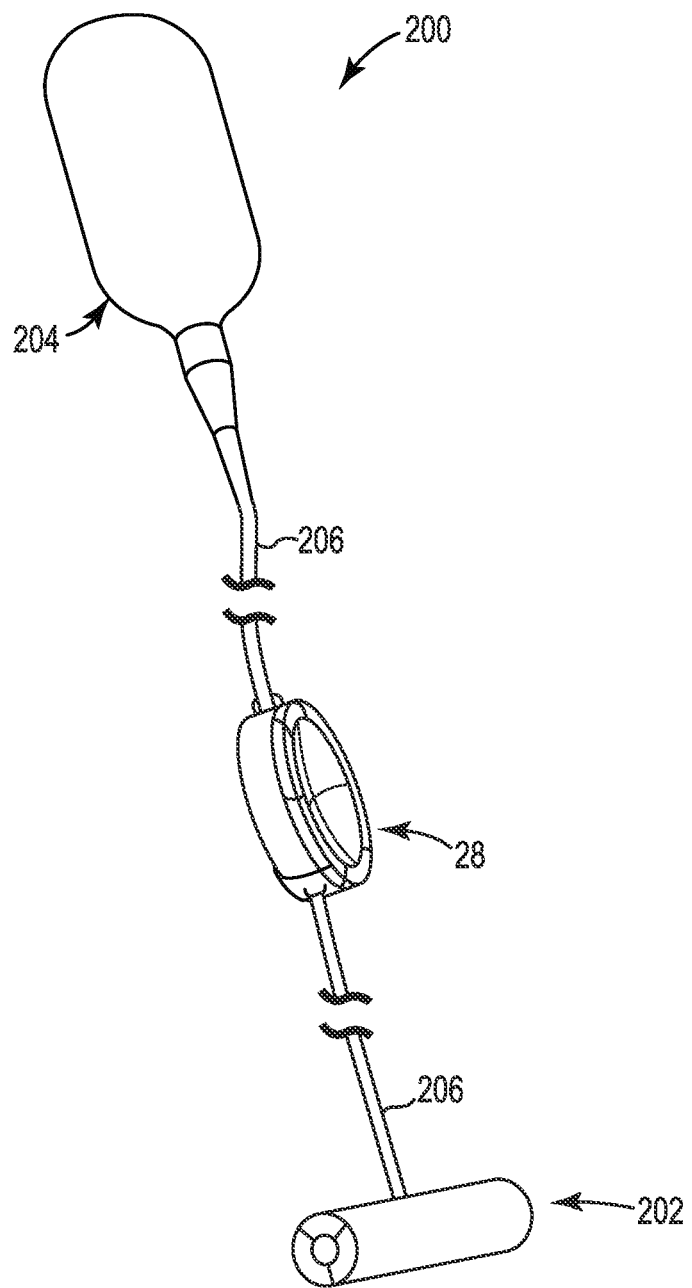
FIG. 11 is a perspective view of one embodiment of an artificial urinary sphincter system.

FIG. 11 is a perspective view of one embodiment of an artificial urinary sphincter (AUS) system 200 useful in treating urinary incontinence. The system includes a cuff 202 that is implantable around a portion of a urethra, an implantable pressure-regulating reservoir 204, and the deflation assembly 28 or 100 described above that is attachable between the cuff 202 and the implantable pressure-regulating reservoir 204, for example by kink-resistant tubing 206. The system 200 obviates the use of the usual pump that is employed with the usual AUS systems.

The cuff 202 is implanted around the urethra and the pressure-regulating reservoir 204 is provided to pressurize the closed system 200 to suitable pressures that will coapt the urethra (e.g., 50-80 cm $H_2O$). The deflation assembly 28 is operable to selectively restrict movement of the fluid from the cuff 202 to the pressure-regulating reservoir 204. In certain configurations the deflation assembly 28 configures the system 200 to have substantially equal pressure in the cuff 202 and the reservoir 204, for example when the cuff 202 coapts the urethra. In another configuration, the deflation assembly 28 configures the system 200 to have a lower pressure in the cuff 202 and a higher pressure in the reservoir 204, for example when the cuff 202 is deflated to open the urethra to allow the user to pass urine.

The cuff 202 is implanted around the bulbous urethra or around the portion of the urethra descending from the bladder neck. The cuff 202 is sized to allow placement as close to the bladder as possible (desired by some surgeons), or positioned distal the bladder neck as suitably determined by the surgeon. The cuff 202 is generally about 2 cm wide and have varying lengths suited to different anatomical sizes, where the lengths are provided in a range from 4-11 cm.

The pressure-regulating reservoir 204 is provided as a balloon or other suitable flexible container and is usually implanted in the abdomen or prevesical space. In one embodiment, the pressure-regulating reservoir 204 is fabricated from silicone elastomer and is pressurized in a range of 50-80 cm $H_2O$ when implanted and attached to the components of the system 200.

Figure 12:
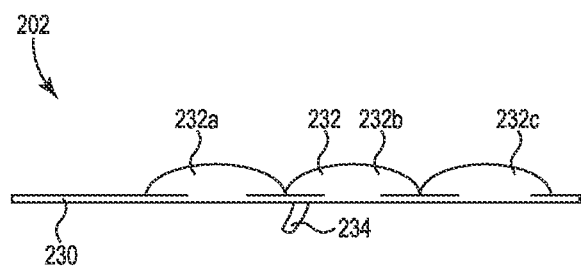
FIG. 12 is a side view and FIG. 13 is a top view of one embodiment of a cuff of the system illustrated in FIG. 11.
Figure 13:
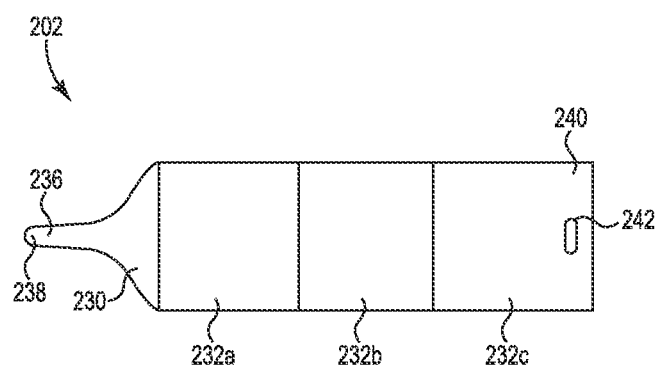

FIG. 12 is a side view and FIG. 13 is a top view of one embodiment of the cuff 202. The cuff 202 illustrated in FIG. 11 is in its implanted configuration, whereas the cuff 202 illustrated in FIG. 12 is in its pre-implantation state.

The cuff 202 includes an expanding bladder portion 232 attached to a base 230. A connector 234 is provided on the base 230 for connection with the tube 206 (FIG. 11), and the connector 234 communicates with the bladder portion 232. In one embodiment, the bladder portion 232 is provided as a series of segments or pillows 232a, 232b, 232c that are configured to expand and inflate as liquid is directed into the cuff 202 through the connector 234. In one embodiment, three of the segments or pillows are provided to allow the base 230 to be bent/folded or directed around the circumference of the urethra such that when the pillows 232 expand, substantially uniform pressure is applied to the urethra. The bladder portion 232 may include more than three or fewer than two segments or pillows.

In one embodiment, the base 230 extends from a first end portion 236 provided with a tab 238 to a second opposing end portion 240 provided with a slot 242. Inserting the tab 238 into the slot 242 forms the cuff 202 into a substantially circular configuration configured for encircling the urethra of the user. Movement of liquid through the connector 234 inflates the bladder portion 232, which is useful in inflating the cuff 202 to coapt the urethra to provide the user with a continent state.

Figure 14:
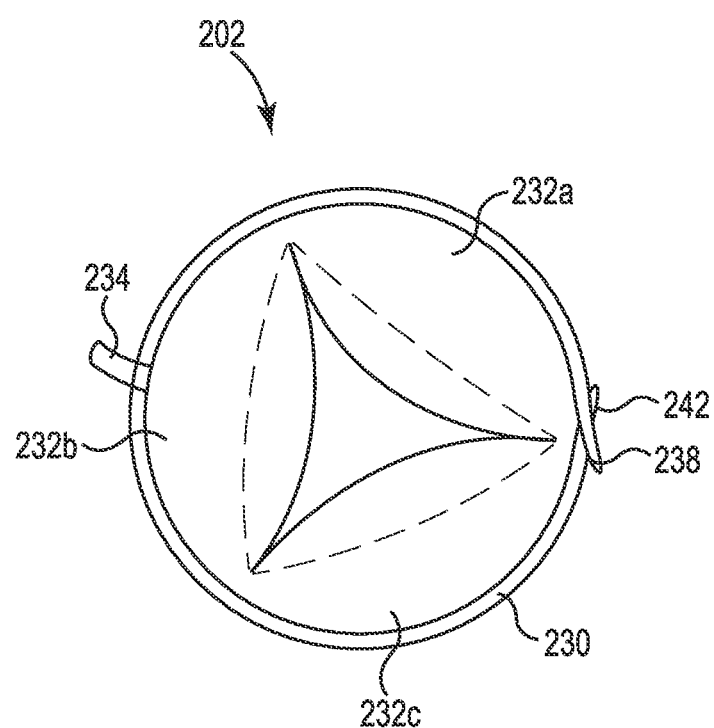
FIG. 14 is an end view of the cuff illustrated in FIGS. 12 and 13 in a circular configuration.

FIG. 14 is an end view of the cuff 202 with the tab 238 inserted into the slot 242 to form the cuff 202 into a substantially circular shape. The cuff 202 may thus be manipulated for placement around the urethra. When the cuff 202 is deflated (as illustrated by the dotted lines), the bladder portion 232 is deflated to remove or diminish pressure applied to the urethra, which allows the urethra to open and pass urine. In contrast, when the cuff 202 is inflated (as illustrated by the solid lines), the bladder portion 232 is inflated to apply pressure against the urethra to coapt the urethra and provide the user with a comfortable, continent state. In one embodiment, the cuff 202 is inflated to a pressure in the range of 50-80 cm $H_2O$ to coapt the urethra.

The cuff 202 is generally fabricated from synthetic material that is suitable for implantation into the human body and configured to retain a volume of liquid (for example when the bladder portion 32 of the cuff 202 is inflated). Suitable materials for fabricating the cuff 202 include silicone, flexible block copolymers, polyolefin, polybutylene, polyurethane, or mixtures or suitable copolymers of the synthetic materials.

Figure 15:
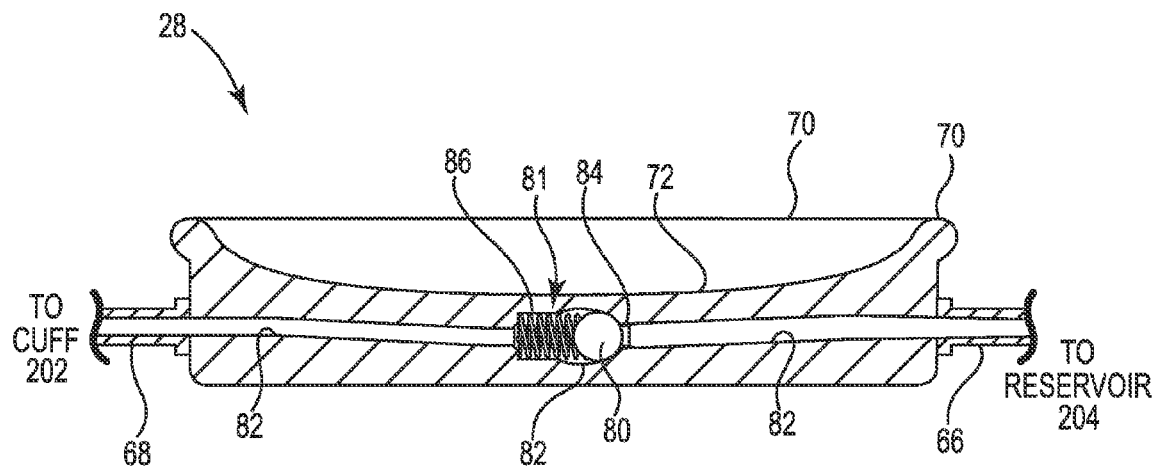
FIG. 15 is a cross-sectional view of one embodiment of a deflation assembly of the system illustrated in FIG. 11.

FIG. 15 is a cross-sectional view of the deflation assembly 28. The deflation assembly 28 is similar to the deflation assembly 28 described above (FIG. 5) and is connected between the cuff 202 and the reservoir 204 (FIG. 11). When implanted and the system 200 is pressurized, the inlet port 66 of the deflation assembly 28 is connected to the reservoir 204 and the outlet port 68 is connected to the cuff 202. In one embodiment, the valve assembly 81 includes the valve 80 that is biased against the seat 84 by the spring 86, where the valve assembly 81 is located in the flow path 82. In one embodiment, the deflation assembly 100 described above (FIGS. 10A and 10B) is suitable as the AUS deflation assembly illustrated in FIG. 11.

The system 200 illustrated in FIG. 11 has at least two states, a continent state and a urine discharge state. In the continent state, the cuff 202 and the reservoir 204 are maintained at an equilibrium pressure that causes the cuff 202 to coapt the urethra and provide the user with continence. In the urine discharge state, the user will palpate the outer peripheral rim 70 which assists in locating the pad 72. Compression applied to the pad 72 deflects or moves the valve 80 off of the seat 84. Pressure applied to the cuff 202, for example by the hand of the user pressing against the skin in the perineal area, will increase the pressure in the cuff 202 and drive the fluid from the cuff 202 through the valve assembly 81 and increase the pressure in the reservoir 204. The increased pressure in the reservoir 204 is maintained by the valve 80 when biased against the seat 84 by the spring 86. As a consequence of the liquid moving from the cuff 202 into the reservoir 204, the cuff 202 deflates which allows the user to pass urine. After the user passes urine, the user will again press the pad 72, and the pressure applied to the pad 72 will move the valve 80 off of the seat 84 and allow the pressure to equalize between the reservoir 204 and the cuff 202.

Figure 16:
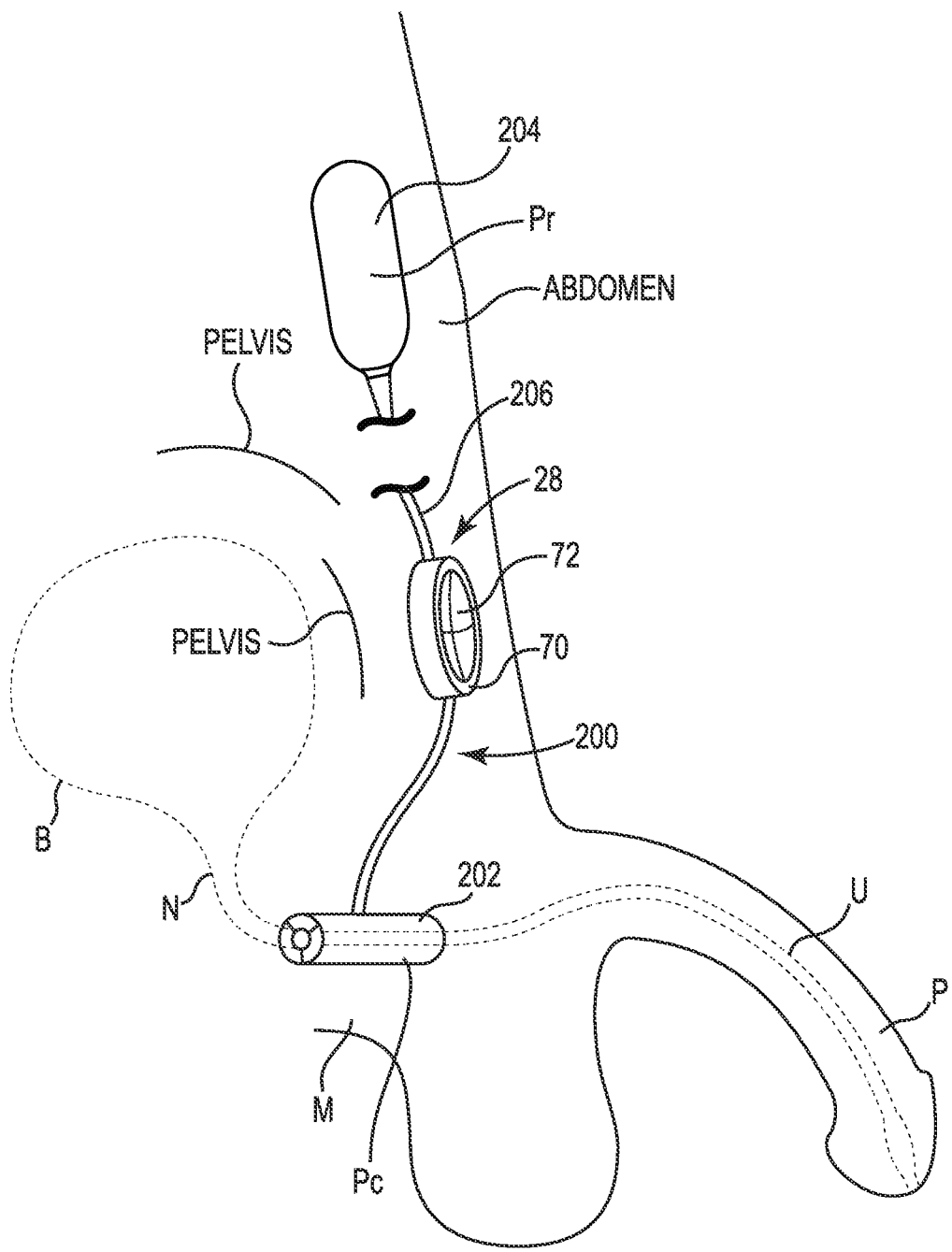
FIG. 16 is a schematic view of one embodiment of the system illustrated in FIG. 11 implanted in the environment of a male user for treatment of urinary incontinence.

FIG. 16 is a schematic view of the system 200 implanted into a male user. The implantation of the system 200 in accordance with the instructions for use will follow the approved surgical procedures as established by the hospital or medical facility. Typically, the patient is brought into an operating room and prepared for surgery by appropriately cleaning and preparing the surgical site (e.g., the perineal area).

For placement of the cuff 202 in the region of the bulbous urethra, a perineal approach is employed that includes placing the patient in a lithotomy position, prepping and draping the patient, and then forming a perineal incision. Tissue is dissected within the perineal incision to access the region around the bulbous urethra. The cuff 202 is primed with liquid and placed around a portion of the urethra downstream from the neck N of the bladder B. Some surgeons have a preference to place the cuff 202 at that location where the urethra U transitions from a vertical arrangement near the neck N of the bladder B to a horizontal arrangement adjacent the perineal area that is associated with substantial protective muscle M mass.

The reservoir 204 is prepared and primed with liquid and implanted in the abdominal region of the patient, for example in a prevesical space as selected by the surgeon.

The deflation assembly 28 is prepared for implantation and primed with liquid prior to having the inlet port 66 connected to the tubing extending to the reservoir 204 and the outlet port 68 connected to the tubing extending to the cuff 202. The act of priming the cuff 202, the reservoir 204, and the deflation assembly 28 (i.e., "primed") includes pressurizing the system 200 to an equilibrium pressure that is suitable for closing the cuff 202 around the urethra to provide the user with a continent state.

The deflation assembly 28 is connected between the cuff 202 and the reservoir 204 and is implanted under the skin in front of (i.e., exterior to) the pelvis. Suitable locations for implantation of the deflation assembly 28 include those described above related to the penile prosthetic, such as between the transversalis fascia and an exterior surface of the pelvis, or behind the puborectalis muscle of the patient. Other suitable locations for implantation of the deflation assembly 28 include placing the base of the deflation assembly 28 against an iliac fossa of the pelvis, or against an iliac crest of the pelvis, or against the pelvis between an anterior gluteal line and an iliac crest of the pelvis so that the pad 72 projects outward for easy access by the user. Some AUS users have limited dexterity, and still other users have a body mass index of greater than 30, both conditions of which can limit the user's ability to operate the cuff 202 for passing urine and for creating the continent state. The system 200 provides an ectopically placed deflation assembly 28 having a pad 72 that is easily palpatable and accessible for operation of the cuff 202.

With the system 200 implanted, the user is provided with a continent state where the system has an equilibrium pressure (between 50-80 cm of water) where the pressure in the cuff 202 is substantially equal to the pressure in the reservoir 204. The pressure in the cuff 202 is selected to be sufficient to coapt the urethra.

When the user desires to void urine, the user presses on the pad 72 to selectively allow liquid to flow from the cuff 202 into the reservoir 204. The flow of the liquid from the cuff 202 is assisted by the user applying pressure to the perineal area to compress the cuff 202 and drive the liquid from the cuff 202 through the deflation assembly 28 and into the reservoir 204. The cuff deflates. The deflation assembly 28 maintains the pressure reservoir 204 at a higher pressure than the cuff 202. The user passes urine. Thereafter, to return to the continent state, the user presses on the pad 72 to allow the deflation assembly 28 to permit liquid to flow from the reservoir 204 back into the cuff 202. The pressure is equalized between the cuff 202 and the reservoir 204, which allows the cuff 202 to coapt the urethra.

Embodiments provide a method of treating urinary incontinence, where the method includes implanting a cuff around a portion of a urethra; coupling the cuff to a reservoir and a deflation assembly, where the deflation assembly is located between the reservoir and separate from the cuff; and implanting the deflation assembly between transversalis fascia and an exterior surface of a pelvis of the patient. One method includes implanting a base of the deflation assembly against a pubic bone of the pelvis. One method includes positioning a pad of an activation surface of the deflation assembly away from the pelvis and so positioned to allow the patient to palpate the pad through skin.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An artificial urinary sphincter system comprising:
a cuff implantable around a portion of a urethra;
an implantable pressure-regulating reservoir; and
a deflation assembly attachable between the cuff and the implantable pressure-regulating reservoir, the deflation assembly comprising:
a valve that selectively restricts movement of a fluid from the cuff to the pressure-regulating reservoir,
a base and an activation surface opposite the base, the activation
surface including an outer peripheral rim surrounding a pad that is
movable to displace the valve to allow the fluid to flow from the cuff to the pressure-regulating reservoir;
wherein an entirety of the pad is recessed relative to the outer peripheral rim such that the outer peripheral rim defines a maxima of the activation surface.

2. The system of claim 1, wherein the deflation assembly is separate from the pressure-regulating reservoir and separate from the cuff.

3. The system of claim 1, wherein the pad is recessed in a concave configuration relative to the outer peripheral rim.

4. The system of claim 1, wherein the pad is a diaphragm connected to the outer peripheral rim.

5. The system of claim 1, wherein the valve is a ball valve.

6. The system of claim 1, wherein the valve is a stem valve having a prong that extends from the pad toward the base of the deflation assembly, the prong movable and so configured to displace an interface between the valve and a flow path in which the valve is seated.

7. The system of claim 1, wherein the outer peripheral rim is rigid and so configured to allow a user to palpate the pad through skin.

8. The system of claim 1, wherein the base of the deflation assembly is a lower surface and the activation surface is an upper surface and the deflation assembly further comprises a side surface extending between the lower surface and the upper surface, the side surface including an inlet port communicating with the pressure-regulating reservoir and an outlet port communicating with the cuff.

9. The system of claim 8, wherein the activation surface includes a length and a width, and the length of the activation surface is larger than a height of the side surface extending between the lower surface and the upper surface.

10. The system of claim 8, wherein the activation surface includes a length and a width, and the width of the activation surface is larger than a height of the side surface extending between the lower surface and the upper surface.

11. The system of claim 8, wherein the activation surface includes a length and a width, and the length and the width are each larger than a height of the side surface extending between the lower surface and the upper surface.

12. The system of claim 1, wherein the pad is movable toward the base and the outer peripheral rim is substantially immovable.

13. The system of claim 1, wherein the artificial urinary sphincter system is characterized by an absence of a pump.

14. An artificial urinary sphincter system comprising:
a cuff implantable around a portion of a urethra;
a pressure-regulating reservoir; and
a deflation assembly separate from the pressure-regulating reservoir and separate from the cuff, the deflation assembly connectable between the cuff and the pressure-regulating reservoir, the deflation assembly enclosing a valve that selectively restricts movement of a fluid from the cuff to the pressure-regulating reservoir;
wherein the deflation assembly comprises a base and an activation surface opposite the base, the activation surface including an outer peripheral rim and a pad that is recessed in a concave configuration relative to the outer peripheral rim such that the outer peripheral rim defines a maxima of the activation surface;
wherein the pad is movable to displace the valve to allow movement of the fluid from the cuff to the pressure-regulating reservoir.

15. An artificial urinary sphincter system comprising:
a cuff implantable around a portion of a urethra;
a pressure-regulating reservoir; and
a deflation assembly separate from the pressure-regulating reservoir and separate from the cuff, the deflation assembly connectable between the cuff and the pressure-regulating reservoir, the deflation assembly enclosing a valve that selectively restricts movement of a fluid from the cuff to the pressure-regulating reservoir;
wherein the deflation assembly comprises a base and an activation surface opposite the base, the activation surface including an outer peripheral rim and a pad that is recessed in a concave configuration relative to the outer peripheral rim;
wherein the pad is movable to displace the valve to allow movement of the fluid from the cuff to the pressure-regulating reservoir;
wherein the artificial urinary sphincter system is characterized by an absence of a pump.

16. The system of claim 15, wherein the outer peripheral rim defines a maxima of the activation surface that allows a user to palpate the outer peripheral rim when depressurizing the cuff.

17. An artificial urinary sphincter system comprising:
a cuff implantable around a portion of a urethra;
a body-implantable pressure-regulating reservoir provided to pressurize fluid contained in the system; and
a deflation assembly attachable between the cuff and the body-implantable pressure-regulating reservoir, the deflation assembly comprising:
an activation surface including a pad recessed relative to a rim of the activation surface; and
a valve located between a base of the deflation assembly and the recessed pad, the valve provided to selectively restrict movement of the fluid in the cuff from moving to the pressure-regulating reservoir;
wherein the recessed pad is movable to displace the valve to allow movement of the fluid from the cuff to the pressure-regulating reservoir.

18. The system of claim 17, wherein the activation surface including an outer peripheral rim and the recessed pad is recessed in a concave configuration relative to the outer peripheral rim.

19. The system of claim 18, wherein the outer peripheral rim defines a maxima of the activation surface.

* * * * *